United States Patent [19]
Gross et al.

[11] Patent Number: 5,082,723
[45] Date of Patent: Jan. 21, 1992

[54] OSMOTICALLY ENHANCED ABSORBENT STRUCTURES

[75] Inventors: James R. Gross, Appleton; Ronald S. Harland, Neenah, both of Wis.

[73] Assignee: Kimberly-Clark Corporation, Neenah, Wis.

[21] Appl. No.: 413,149

[22] Filed: Sep. 27, 1989

[51] Int. Cl.$^5$ .............................................. B32B 5/16
[52] U.S. Cl. ..................................... 428/283; 428/284; 428/297; 428/323; 428/372; 428/376; 428/398; 428/401; 428/402; 428/403; 428/913; 604/367; 604/368
[58] Field of Search ............... 428/372, 376, 283, 221, 428/913, 364, 402, 403, 284, 398, 379, 401, 297, 913; 604/367, 368

[56] References Cited

U.S. PATENT DOCUMENTS

| | | | |
|---|---|---|---|
| 3,073,309 | 1/1963 | Mosier | 128/290 |
| 3,121,427 | 2/1964 | Mosier | 128/284 |
| 3,419,345 | 12/1968 | Parrish | 8/137.5 |
| 3,551,410 | 12/1970 | MacDonald | 260/212 |
| 3,574,132 | 4/1971 | Mosier | 252/316 |
| 3,666,678 | 5/1972 | Mosier et al. | 252/316 |
| 3,676,363 | 7/1972 | Mosier | 252/316 |
| 3,926,891 | 12/1975 | Gross et al. | 260/29.6 E |
| 3,935,099 | 1/1976 | Weaver et al. | 210/43 |
| 4,043,952 | 8/1977 | Ganslaw et al. | 260/17.4 ST |
| 4,177,056 | 12/1979 | Mueller | 71/93 |
| 4,186,238 | 1/1980 | Holst | 428/326 |
| 4,277,582 | 7/1981 | Mueller et al. | 525/421 |
| 4,473,670 | 9/1984 | Kessidis et al. | 523/105 |
| 4,492,720 | 1/1985 | Mosier | 427/213.3 |
| 4,541,871 | 9/1985 | Obayashi et al. | 106/197.2 |
| 4,666,975 | 5/1987 | Yamasaki | 524/733 |
| 4,666,983 | 5/1987 | Tsubakimoto | 525/119 |
| 4,686,776 | 8/1987 | Matsuhara | 34/95 |
| 4,693,713 | 9/1987 | Chmelir | 604/368 |
| 4,735,987 | 4/1988 | Morita et al. | 524/436 |
| 4,742,086 | 5/1988 | Masamizu et al. | 521/62 |
| 4,767,825 | 8/1988 | Pazos et al. | 525/408 |
| 4,783,510 | 11/1988 | Saotome | 525/329.7 |
| 4,814,182 | 3/1989 | Graham et al. | 424/484 |
| 4,819,342 | 4/1989 | Matsubara et al. | 34/95 |
| 4,820,293 | 4/1989 | Kamme | 604/368 |

FOREIGN PATENT DOCUMENTS 62-212404 9/1987 Japan.

Primary Examiner—James J. Bell
Attorney, Agent, or Firm—Thomas J. Mielke

[57] ABSTRACT

An absorbent structure of a superabsorbent material which superabsorbent material defines a chamber, said chamber containing an amount of an osmotic material. The presence of the chamber and osmotic material within the chamber has been found to increase the absorptive capacity of the superabsorbent material on a gram per gram basis.

29 Claims, 4 Drawing Sheets

OSMOTICALLY ENHANCED ABSORBENT STRUCTURES

BACKGROUND OF THE INVENTION

1. Field of the Invention

The present invention relates to absorbent structures. Specifically, the present invention relates to an absorbent structure having osmotically enhanced absorption characteristics.

2. Description of the Related Art

The use of water-swellable, water-insoluble polymeric materials as absorbents is known. For example, particles of water-swellable, water-insoluble polymeric materials have been incorporated into batts of wood pulp fluff to increase the absorptive capacity of the batts. Such batts are incorporated into articles such as diapers, sanitary napkins, adult incontinence products and the like. Such water-swellable, water-insoluble polymeric materials are often capable of imbibing many times their weight in water. For example, it is not unusual for one gram of water-swellable, water-insoluble polymeric material to be able to absorb more than 10 grams of a liquid. Thus, such water-swellable, water-insoluble polymeric materials are commonly, and will hereinafter be, referred to as superabsorbent materials, incorporation of such superabsorbent materials into absorbent batts significantly increases the absorptive capacity of the batts.

When such superabsorbent materials are incorporated into absorbent batts, which batts are placed in absorbent products such as diapers, it is also desirable that the superabsorbent materials be able to retain an absorbed liquid when a modest amount of pressure is applied to the superabsorbent material. Additionally, it is desired that the superabsorbent materials be able to imbibe a liquid in a rapid manner. Unfortunately, in the absence of geometric influences, the rate at which superabsorbent materials can imbibe a fluid is generally inversely related to the ability of the superabsorbent materials to swell. That is, the higher the equilibrium swelling of a superabsorbent material, the slower the rate of uptake.

Compared to the absorbent batts in which the superabsorbent materials may be incorporated, the superabsorbent materials are relatively expensive. Therefore, when it is desired to employ the superabsorbent materials in an absorbent product and minimize the ultimate cost of the absorbent product, it is desirable to minimize the amount of superabsorbent material present in the product while maintaining the performance of the product. Accordingly, several attempts have been made to optimize various liquid absorbing characteristics of known water-swellable polymers.

For example, Japanese Kokai Patent No. SHO 62[1987]-212404 published Sept. 8, 1987, is directed to the preparation of highly water-swellable polymers. The polymeric materials are prepared by emulsion polymerization of monomers known to form superabsorbent materials in the presence of monosaccharides and/or oligosaccharides and a crosslinking agent. Such a polymerization process is described as producing polymeric materials which are grafted onto the mono and/or oligosaccharides. The polymers are described as having an improved absorption rate; moreover, reference to Table 1 of the Japanese publication indicates that the absorption capacity is similarly improved.

U.S. Pat. No. 4,541,871, issued Sept. 17, 1985, to Obayashi et al. describes a two-step process for preparing crosslinked carboxylic acid salt-containing polymers. According to the process, a lightly or even non-crosslinked polymer is slightly swollen and then further crosslinked with a difunctional material reactive with carboxylate groups. This process is described as producing a polymer particle which is more highly crosslinked on the outer surface then on the interior thereof. The particles are described as being capable of more rapid wetting without clumping or gel blocking.

U.S. Pat. No. 4,783,510, issued Nov. 5, 1988, to Saotome is directed to a process for improving a water absorbent poly(acrylic acid) and an improved polymer produced by said process. The process involves contacting a water absorbent poly(acrylic acid) with an aqueous solution containing a water soluble peroxide radical initiator. This contacting step is followed by heating which causes substantially only the surface portion of the polymer to undergo crossling with the radical initiator while leaving the remaining core portion of the polymer substantially intact. The polymer so produced is described as being excellent in both water absorbency and water absorption rate.

U.S. Pat. No. 4,693,713 issued Sept. 15, 1987, to Chmelir et al. is directed to an absorbent for blood and serous body fluids. The absorbents comprise a mixture of a superabsorbent material and a water soluble compound such as methylurea, monosaccharides, inorganic acids, salts of mono or poly-carboxylic acids and the like. The presence of the second component is described as acceerating the capillary flow of blood through a mass of the particulate absorbent component, thereby increasing the rate of absorption of the mixture.

In a similar manner, but for a different purpose, U.S. Pat. No. 4,473,670 issued Sept. 25, 1984, to Kessidis is directed to a salt-filled absorbable polymer. The absorbable polymer described by Kessidis is one which is capable of being metabolized by a living organism. That is, the polymers are capable of being placed in a living organism and subsequently dissolved and absorbed by the organism. Kessidis describes the use of a finely divided filler of sodium chloride or potassium chloride in such absorbable polymers to increase the rate of absorption of such polymers. In use, the filler material is quickly dissolved creating more surface area for enzymatic attack and quicker decomposition of the polymer in a biological system.

Similarly, U.S. Pat. No. 3,121,427, issued Feb. 18, 1964, to Mosier describes a catamenial appliance. In connection with the catamenial appliance, Mosier describes a mixture of a gelling agent, such as gelatin and/or agar-agar and sugar. The mixture of gelling material and sugar is wrapped in a tissue material. Gelling of menses through the gelling materials interacting with the hemoglobin in blood is described as proceeding through osmotic forces. The water-soluble inert filler, sugar or sodium chloride, is described as continuously and rapidly dissolving, thereby exposing fresh surfaces of the gel-forming matrix.

U.S. Pat. No. 4,742,086, issued May 3, 1988, to Masamizu, et al. is directed to a process for manufacturing a porous polymer. Described are polymeric particles containing a plurality of voids in their interior. The particles are described as having a small apparent specific gravity and as being superior in terms of water absorbing properties, permeability, and elasticity.

U.S. Pat. No. 4,686,776 issued Aug. 18, 1987, to Matsubara is directed to a dehydrating device. The device comprises a high osmotic pressure substance, a polymeric water absorber, and a hydrophilic alcohol. The three substances are copresent and integrally covered with a semi-permeable membrane. Water can permeate through the membrane and be absorbed by the polymeric water absorber. The presence of the high osmotic pressure substance is described as increasing the rate of water transport through the semi-permeable membrane.

U.S. Pat. No. 3,419,345 issued Dec. 31, 1968, to Parrish is directed to the neutralization of hydrophilic gel fibers of a cellulose derivative. This reference describes a process by which swellable fibers of a cellulose derivative are neutralized with an aqueous, concentrated, buffered salt solution having a pH within the range of about 5.0 to about 9.0. In this instance the buffered salt solution is employed to act as a base to neutralize the acid functionality and is not described as being used to incorporate salt into the cellulose fibers.

In a similar fashion, but directed to oxidized cellulose, U.S. Pat. No. 3,551,410 issued Dec. 29, 1970, to MacDonald et al. describes increasing the water-retentivity of cellulose fibers and the product produced thereby. MacDonald et al describe that the ability of a carboxyl cellulose to retain water is increased by soaking the carboxyl cellulose in a buffered salt solution.

Several techniques to improve the absorption rate and capacity of the superabsorbent material through chemical means are described. Unfortunately, none of the above references describe or suggest simple means by which the absorptive capacity of a given superabsorbent material can be increased on a gram of absorbed liquid per gram of polymer basis beyond that capacity due to the superabsorbent material itself. The concept of utilizing geometric configurations to increase absorption rate and/or capacity is not described by the references.

SUMMARY OF THE INVENTION

It is desired to provide a superabsorbent material which superabsorbent material possesses an enhanced absorptive capacity on a gram of absorbed solution per gram of superabsorbent material basis (hereinafter "gram per gram basis") and which material is capable of absorbing a liquid in a rapid manner.

It is further desired to provide a method by which the absorptive capacity of superabsorbent materials can be increased on a gram per gram basis beyond that capacity possible for the superabsorbent material itself. By increasing the capacity of the superabsorbent material on a gram per gram basis, a lower amount of the superabsorbent material can be employed in a given absorbent product to obtain a desired degree of absorption. It is further desired to provide a method by which the absorption rate of a superabsorbent material can similarly be increased.

These and other related goals are achieved in an absorbent structure which comprises a superabsorbent material which defines a chamber, which chamber contains an amount of an osmotic material.

In a second aspect, the present invention concerns a method for increasing the absorptive capacity and absorption rate of a superabsorbent material, which method comprises the step of encapsulating an osmotic material with said superabsorbent material.

The absorbent structures according to the present invention are suitably incorporated into a wide variety of absorbent products such as diapers, sanitary napkins, bandages, adult incontinence products, and the like.

BRIEF DESCRIPTION OF THE DRAWINGS

FIG. 2b is a cross-sectional view taken along line 2b–2b of FIG. 2a.

FIG. 3b is a cross-sectional view taken along line 3b–3b of FIG. 3a.

DETAILED DESCRIPTION OF THE PREFERRED EMBODIMENTS

Figure 1A:
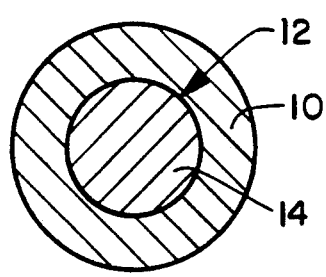
FIGS. 1a–1f are illustrations of alternative embodiments of a preferred embodiment of the present invention in which the structure of the present invention is in particulate form.

The present invention concerns an absorbent structure. Specifically, the present invention concerns a superabsorbent material which material defines a chamber which chamber contains an osmotic material. The presence of the chamber defined by the superabsorbent material in conjunction with the osmotic material contained therein serves to increase the absorptive capacity of the superabsorbent material on a gram per gram basis beyond the capacity possible with the superabsorbent material by itself. Moreover, the presence of the osmotic material within the chamber defined by the superabsorbent material has been found to increase the rate at which the superabsorbent material absorbs a liquid.

Superabsorbent materials suitable for use in the present invention are known to those skilled in the art. Any natural or synthetic superabsorbent material which is capable of absorbing at least about 2 times its weight in water, preferably about 5 times its weight in water, and most preferably about 20 times its weight in water, is suitable for use in the present invention. Exemplary of superabsorbent materials suitable for use in the present invention are gelatin; alginates; cellulose based polymers such as methyl cellulose, hydroxymethyl cellulose, carboxymethylcellulose, cellulose acetate phthalate, and the like; starch based polymers such as carboxymethyl starch; natural gums, such as gum arabic, locust bean gum, carrageenan gum, and xanthan gum; pectins; polymers formed from acid-group containing monomers, such as poly(acrylates) (including poly(acrylic acid), poly(methacrylic acid), and the like), poly (ethers), poly(acrylamides, poly(vinyl alcohol), maleic anhydride copolymers, poly(vinyl sulfonates), hydrolyzed acrylonitrile grafted starch, acrylic acid grafted starch, poly(N-vinyl pyrrolidone), poly(2-hydroxyethylacrylated poly(2-hydroxyethylmethacrylate), poly(sodium acrylate-co-acrylic acid), poly(vinylsulfonic acid), poly(ethyleneoxide), block co-polymers of ethylene oxide with polyamides, polyesters, and polyurethanes, and salt forms mixtures and copolymers of the above.

The superabsorbent material defines a chamber which contains an osmotic material. As used herein, the term "chamber" refers to an area which is substantially void of the superabsorbent material from which said chamber is defined. Thus, reference to the "chamber" is intended to encompass the situation wherein the superabsorbent material defines a chamber which is completely filled with an osmotic material as well as the situation wherein the chamber comprises a portion of osmotic material and a portion of non-omotic material, for example air.

As used herein the term "osmosity" refers to the molar concentration of sodium chloride required to exhibit the same osmotic pressure or freezing point depression as a given solution. Osmosity is expressed in gram-moles per liter. For the purposes of this application, determination of osmosity is accomplished by employing an aqueous solution containing one (1) weight percent of a given material. Thus, the osmosity of sucrose is determined by calculating the molar concentration (g-mol/l) of sodium chloride necessary to produce the same osmotic pressure or freezing point depression as a one (1) weight percent aqueous solution of sucrose. This value is reported in the literature to be 0.015 g-mol/l. The osmosity of sodium chloride is reported as 0.172 g-mol/l, and that of lithium chloride is reported as 0.244 g-mol/l. As used herein the "relative osmosity" of a given material is determined by the formula:

$$\frac{O_1}{O_2}$$

wherein $O_1$ is the osmosity of the material and $O_2$ is the osmosity of sodium chloride (0.172 g-mol/l). Thus, sodium chloride has a relative osmosity of 1 (0.172/0.172), sucrose has a relative osmosity of 0.087 (0.015/0.172) and lithium chloride has a relative osmosity of 1.42 (0.244/0.172).

As used herein, the term "osmotic material" refers to a material having a relative osmosity, as defined above, of at least about 0.05 preferably at least about 0.09 and more preferably at least about 1.0. It is understood that a greater concentration of a material having a relatively low relative osmosity will be required to produce the same osmotic pressure or freezing point depression exhibited by a material having a relatively high relative osmosity. For example, an aqueous solution containing about 11.5 weight percent sucrose will produce the same osmotic pressure or freezing point depression as an aqueous solution containing about 1 weight percent sodium chloride (0.172/0.015 = ~11.5).

Osmotic materials suitable for use in the present invention are those water-soluble or water-dispersible materials which can be formed into the absorbent structures of the present invention and which do not deleteriously affect the superabsorbent materials of the present invention to an unacceptable degree. Suitable examples include but are not limited to the water-soluble or water-dispersible salts of organic or inorganic acids, organic or inorganic acids, long chain alcohols, polyhydric alcohols, urea and urea derivatives, mono- or oligosaccharides, water-soluble polymers, surfactants, and the like. For reasons of cost and availability, it is desirable to select the osmotic material from the group consisting of the water-soluble salts of organic or inorganic acids, organic or inorganic acids, urea and urea derivatives, and mono- or oligosaccharides or the like.

The osmotic material present within the chamber may be in the form of a particulate solid, a low melting point wax, an aqueous or non-aqueous solution or suspension, a gel, a porous solid, or the like. The chamber defined by the superabsorbent material is desirably substantially completely surrounded and encapsulated by the superabsorbent material. In this manner, free flow of the osmotic material out of the absorbent structure is substantially prevented. As will be discussed in greater detail below, in one embodiment of the present invention the absorbent structure is in the shape of a fiber. In this case, when the length to diameter ratio of the fiber is very large (at least about 50:1) the ends of the fiber may be open but are preferably sealed.

The absorptive capacity of superabsorbent materials is generally expressed as the number of grams of a 1.0 weight percent aqueous sodium chloride solution which the superabsorbent materials can absorb per gram of superabsorbent material (gram per gram basis). However, other solutions such as menses, artificial urine or bovine blood may be used. The inventors have discovered that the absorptive capacity, on a gram per gram basis, of a given superabsorbent material can be greatly increased by forming the superabsorbent material into the absorbent structures of the present invention.

Without intending to be bound by a theory, it is believed that the increase in absorptive capacity results from the combination of the chamber defined by the superabsorbent material and the osmotic material present in the chamber. When the superabsorbent materials are exposed to a liquid, the volume of the superabsorbent material increases in proportion to the amount of water absorbed by the superabsorbent material. When the superabsorbent material defines a chamber, it is believed that the chamber similarly expands as the superabsorbent material expands due to absorption of a liquid. Due to the osmotic material present within the chambers, liquid is drawn through the water-swollen superabsorbent material defining the chamber, which liquid then at least partially fills the chamber. As liquid fills the chamber, the osmotic material, if in solid form and soluble in the liquid, goes into solution. As the chamber expands, more and more liquid can be drawn through the superabsorbent material into the chamber until equilibrium is reached. Thus, the absorptive capacity per gram of superabsorbent material is increased. This results from the fact that at least a portion of the absorbed liquid is physically present as a liquid in the chamber. When the superabsorbent materials are formed into structures defining no osmotic material-containing chambers, as in the prior art, only that liquid which is maintained within the molecular structure of the superabsorbent material is capable of being held by the superabsorbent material. It is believed that it is the amount of liquid which is maintained within the chambers of the structures of the present invention which represents the increased capacity achieved by the structures of the present invention.

In another aspect, the presence of the osmotic material within the chamber defined by the superabsorbent material causes the superabsorbent material to absorb liquid at a more rapid rate. It is similarly hypothesized that this rapid absorption is due to the osmotic pressures acting on the superabsorbent materials of the present invention.

When superabsorbent materials are to be employed in personal care products such as diapers it is generally desireable to employ a superabsorbent possessing both a high capacity and a high gel strength or stiffness. High capacity is desired because it allows for the use of a smaller mass of superabsorbent material. High gel strength or stiffness is desireable to prevent the formation of flowable gelatinous masses of superabsorbent which may leak from the product or form a barrier to transport of liquids through the matrix in which such superabsorbent materials are generally located.

As a general rule, the capacity of a superabsorbent material (on a gram per gram basis) is inversely related to the gel strength or stiffness of the superabsorbent material. That is, a superabsorbent material having a capacity of 20 grams per gram will generally have a gel stiffness or strength below that of a superabsorbent material having a capacity of 10 grams per gram. Naturally, it is generally desirable to employ a superabsorbent material having a high capacity and a high gel strength or stiffness. In the past it has been necessary to balance these two variables sacrificing capacity for sufficient gel strength to prevent the problems discussed above.

According to the present invention, the capacity of superabsorbent materials can be dramatically increased (on a gram per gram basis). Thus, superabsorbent materials that have, in the past, been considered to possess too low a capacity for use in personal care products may be formed into the structures of the present invention thus having their capacity raised to the level at which they are suited for use in personal care products. Use of such superabsorbent materials may have the added benefit of possessing gel strengths which make them particularly well suited for use in personal care products.

It is clear that the chambers defined by the superabsorbent material may vary in size. The ratio, in a non-swollen state, of the volume of the chamber to the volume of the absorbent structure, including the chamber, can vary within wide ranges. Suitably, the ratio of the chamber volume to the volume of the absorbent structure (including the chamber) can be from about 1:10 to about 999:1000, preferably, from about 1:2 to about 9:10. As a general rule the ratio of chamber volume to absorbent structure volume can be controlled by the process and process parameters used during the formation of the absorbent structures of the present invention.

Similarly, the amount of osmotic material present within the chamber can vary depending on the osmotic pressures which it is desired be created as well as the osmotic material employed. As a general rule, the ratio of the volume of osmotic material present in the chamber to the volume of the chamber will be within the range of about 1:100 to about 1:1, preferably of about 1:20 to about 1:1. In one embodiment of the present invention, the chamber is not completely filled with osmotic material and the ratio of the volume of osmotic material present in the chamber to the volume of the chamber is within the range of about 1:100 to about 99:100 preferably, of about 1:20 to about 19:20. The amount of osmotic material present within the chamber can be controlled by the process and process parameters used during the formation of the absorbent structures of the present invention.

The performance of the absorbent structures according to the present invention can be influenced by a number of variables. Exemplary of such variables are the superabsorbent material, osmotic material, chamber volume to absorbent structure volume ratio, osmotic material volume to chamber volume ratio and the process by which the structure is formed. As a general rule, it is desirable that the absorbent structures be tailored to possess a desirable absorptive capacity, size and structural integrity. For example, if a large amount of osmotic material is present within the chamber, the absorbent structures of the present invention may continue to absorb liquid until the point at which the amount of liquid present in the chamber increases such that the superabsorbent material defining the chamber can no longer maintain its structural integrity. Obviously, if the superabsorbent material loses its structural integrity, the liquid maintained within the chamber will be released and the absorptive capacity, on a gram per gram basis, diminished.

The interaction of the above recited variables can be analogized to blowing up a balloon. If too much air is forced into the interior of the balloon, the balloon bursts and the air originally maintained within the balloon is released. Accordingly, it is believed desirable to tailor the described variables such that the absorbent structure does not absorb so much liquid within its chamber that it loses its structural integrity unless, in application, this trait is desired. Clearly, the exact amount of internal pressure which the absorbent structure can sustain is dependent on the strength of the superabsorbent material defining the chamber. One skilled in the art can easily, empirically, determine the particular combination of the above recited variables which produces an absorbent structure suitable for the intended end use.

When the osmotic material present in the absorbent structures of the instant invention are water-soluble, they may have a tendency to diffuse out of the chamber, through the superabsorbent material and into the environment surrounding the absorbent structures. Clearly, if too much of the osmotic material diffuses out of the structures, the improved absorbency characteristics will deteriorate. Accordingly, when a water-soluble osmotic material is employed, it is desirable to select an osmotic material which will not diffuse out of the particles at an undesirably fast rate.

This problem may be reduced, somewhat, depending on the article in which the absorbent structures are incorporated. The most rapid diffusion will occur when the structures are in a flooded liquid environment. When the absorbent structures are not in a liquid environment, the diffusion rate will slow down. Thus, when the absorbent structures of the present invention are present in a diaper, such diffusion occurs most rapidly just after a urine insult and before the liquid has been absorbed by the absorbent present in the diaper. Accordingly, in such an environment, the problem is generally minimized due to the short duration of a flooded liquid environment.

The absorbent structures of the present invention may be formed in a variety of geometric shapes. For example, the structures may be in the form of spheres, rods, irregularly shaped particles, fibers, films, and the like. A number of the specific embodiments possible are illustrated in the drawings.

Figure 1C:
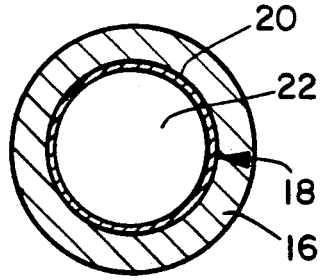
Figure 1E:
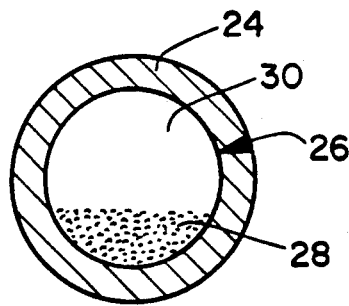
Figure 1B:
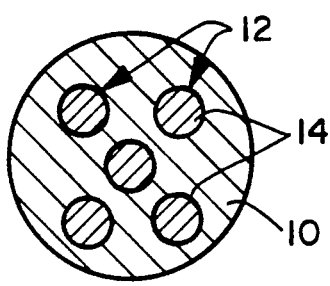

With reference to the drawings, FIGS. 1a–1f represent cross-sectional views of alternative embodiments of a preferred embodiment of the present invention wherein the structure according to the present invention is a particle. In FIG. 1a a superabsorbent material 10 defines a void 12 which is substantially completely (>99%) filled with an osmotic material 14. FIG. 1b illustrates an embodiment similar to FIG. 1a, except the superabsorbent material 10 defines multiple voids 12 which voids are substantially completely filled with an osmotic material 14.

Figure 1D:
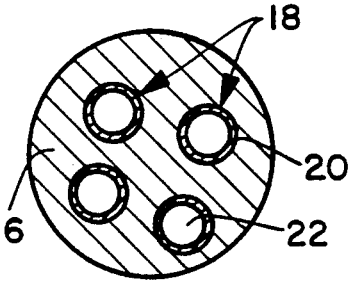

FIG. 1c illustrates the situation wherein a superabsorbent material 16 defines a void 18 which is only partially filled with an osmotic material 20. The osmotic material 20 is in the form of a coating along an interior surface of the void 18. Since the osmotic material only partially fills the void 18, an area 22 substantially free of any osmotic material is formed. FIG. 1d illustrates an embodiment similar to FIG. 1c except the superabsorbent material 16 defines multiple voids 18 which voids are only partially filled with the osmotic material 20. Again, the osmotic material 20 is in the form of a coating along an interior surface of the void 18 and defines an area 22 which is substantially free of any osmotic material. It is understood that the area void of any osmotic material may be filled with a gas, liquid or solid.

Figure 1F:
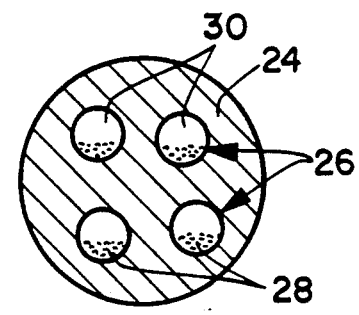

FIG. 1e illustrates the situation wherein the superabsorbent material 24 defines a void 26 which is only partially filled with an osmotic material 28. The osmotic material 28 is in the form of one or more particles. Again, since the osmotic material 28 only partially fills the void 26, an area 30 substantially free of any osmotic material is formed. FIG. 1f illustrates an embodiment similar to FIG. 1e except the superabsorbent material 24 defines multiple voids 26 which voids are only partially filled with an osmotic material 28. The osmotic material 28 is in the form of one or more particles and only partially fills the void 26, thus defining area 30 which is substantially free of any osmotic material.

Figure 2A:
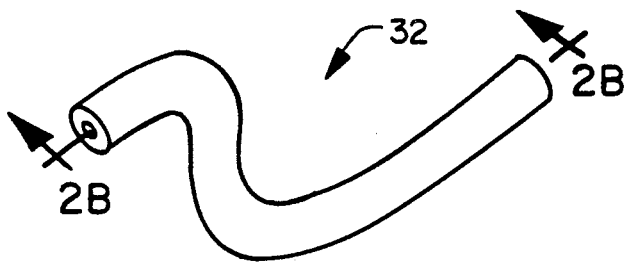
FIG. 2a is an illustration of a structure according to the present invention in the form of a fiber.
Figure 2B:
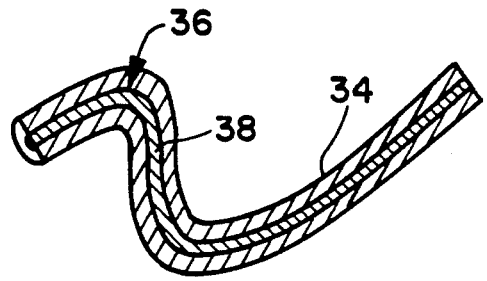

FIG. 2a illustrates the situation wherein the absorbent structure of the present invention is in the form of a filled fiber 32. As can be seen from reference to FIG. 2b (which is a cross-sectional view of FIG. 2a) a superabsorbent material 34 defines a void 36 running through the length of the fiber. The void 36 is substantially completely filled with an osmotic material 38. While FIGS. 2a and 2b illustrate that the void 36 is filled and the ends of the fiber open, it is understood that the void need not be completely filled and that the ends of the fiber may be sealed.

Figure 3A:
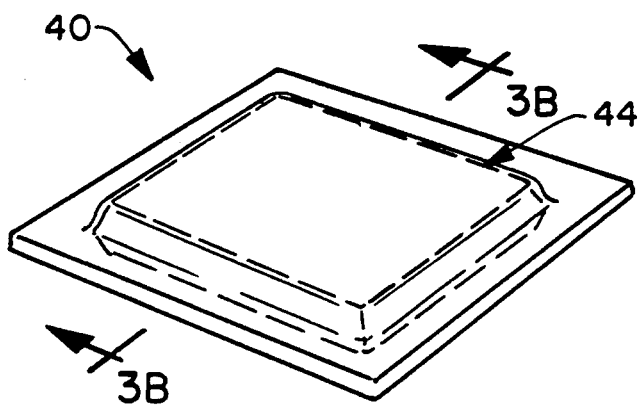
FIG. 3a is an illustration of a structure according to the present invention in the form of a film laminate pouch.
Figure 3B:
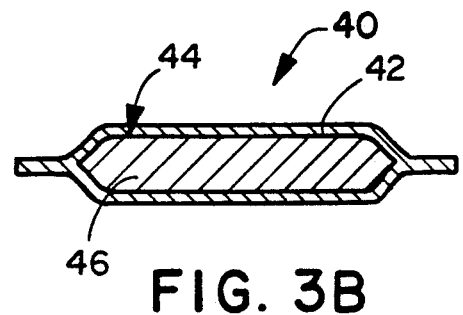

FIG. 3a illustrates the situation wherein the absorbent structure of the present invention is in the form of a film laminate pouch 40. As can be seen from reference to FIG. 3b (which is a cross-sectional view of FIG. 3a) a superabsorbent material 42 defines a void 44 which is substantially completely filled with an osmotic material 46. Again, it is to be understood that the void need not be completely filled with osmotic material.

When the structures are formed in the shape of spheres or irregularly shaped particles the structures will, suitably, have an average diameter, in the unswollen state, of from about 1 micron to about 4000 microns preferably from about 50 microns to about 1000 microns. When the structures are formed in the shape of fibers, the fibers will suitably have a length to diameter ratio of from about 5:1 to about infinity:1 (continuous fiber) and may have a length of, for example, from about 1 millimeter to about 25 millimeters.

As discussed above, in one embodiment of the present invention the absorbent structures comprise a chamber which is generally completely filled with an osmotic material (chamber volume to osmotic material volume of about 1:1). Such structures are suitably formed by providing a solid particle of an osmotic material which particle is then coated with a superabsorbent material to completely encapsulate said osmotic material. Exemplary of one method for forming such absorbent structures is to spray a coating of superabsorbent material onto individual particles of osmotic material. Alternatively, the superabsorbent material could be dissolved in a solvent and deposited on an osmotic material which is generally insoluble in said solvent. Or, such an absorbent structure can be formed through an inverse suspension polymerization process as set forth in greater detail in the examples.

As discussed above, in another embodiment of the present invention the absorbent structures may comprise a superabsorbent material defining a chamber which chamber is not completely filled with an osmotic material (ratio of volume of osmotic material to volume of chamber is less than 1:1). That is, the chamber may contain an amount of an osmotic material and an amount of a non-osmotic material, such as, for example, air. Such an absorbent structure may be formed, for example, by coating a porous or hollow particle of osmotic material with a superabsorbent material. If formed in such a manner, the absorbent structure would have a chamber which is partially filled with an osmotic material and which is partially filled with air. It is hypothesized that several advantages may be achieved by forming such an absorbent structure.

First, as described above, it is possible that when the chamber is completely filled with an osmotic material the absorbent structure may burst upon swelling if too much liquid is taken into the chamber. If a potion of the chamber is filled with a non-osmotic material this problem may be somewhat reduced. This rupture could result for several reasons. First, if the superabsorbent material is more permeable to the non-osmotic material, the non-osmotic material may diffuse out of the chamber thus allowing more liquid to pass into the chamber without increasing the pressure within the chamber. Additionally, if the presence of a given size chamber which is completely filled with an osmotic material is found to cause the absorbent structures to burst, substituting an equivalently sized chamber which is only partially filled with an osmotic material may allow the absorbent structures to swell to equilibrium without bursting since lower osmotic forces will be created within the chamber thus causing less water to pass into said chamber at equilibrium.

In addition to coating a porous or hollow particle of osmotic material with a superabsorbent material as described above, such absorbent structures may be formed by incorporating a gas-generating species (blowing agent) in the osmotic material which forms the core. The gas generating species is activated by raising the temperature of the structure.

In another preferred embodiment of the present invention, the absorbent structures are in the form of fibers. The fibers define a chamber which chamber contains an osmotic material. The fibers suitably have a length to diameter ratio of at least about 5:1. Such absorbent structures can be formed by filling a hollow fiber with an osmotic material and sealing both ends of the fiber. Alternatively, such structures can be formed by extruding or otherwise coating a superabsorbent material on a fiber of osmotic material. For example, if the osmotic material employed is a thermoplastic water-soluble polymer, such polymer may be extruded in the form of a fiber which fiber is then coated with a superabsorbent material. In a second aspect, the present invention concerns a method for increasing the absorbent capacity of a superabsorbent material. The method involves encapsulating an amount of an osmotic material with the superabsorbent material. As discussed above, the presence of the encapsulated osmotic material serves to greatly improve the absorbent capacity of the superabsorbent material. The specific means by which the osmotic material can be encapsulated by the superabsorbent material have been discussed above and will be further discussed in connection with the examples which follow. Any method suitable for encapsulating an osmotic material with a superabsorbent material is suitable for use in the present invention.

The absorbent structures of the present invention are suitably incorporated into personal care products such as diapers, sanitary napkins, adult incontinent garments and the like. Diapers generally comprise an outer material formed from a generally water-impervious material; an absorbent web adjacent said outer material; and a body-side material adjacent the web of absorbent material, which body-side material is adapted to contact the skin of the wearer. In use, a body fluid such as urine, insults the body-side material, passes through said material and is absorbed into the web of absorbent material. The outer material prevents the absorbed liquid from passing out of the diaper structure. The absorbent structures of the present invention are suitably incorporated into the absorbent web in an amount of from about 5 to about 100 weight percent, preferably from about 5 to about 50 weight percent, based on total absorbent web weight. Diapers and similar products are generally described in U.S. Pat. Nos. 4,798,603 issued Jan. 17, 1989, to Meyer et al.; 4,710,187 issued Dec. 1, 1987, to Boland et al.; 4,762,521 issued Aug. 9, 1988, to Roessler et al.; and 4,770,656, issued Sept. 13, 1988, to Proxmire et al., which references are incorporated herein by reference.

The present invention can best be understood by reference to the following examples (including comparative examples) which examples are not intended to limit, in any way, the scope of the invention as set forth in the claims.

EXAMPLE 1

Absorbent structures according to the present invention may be produced through the inverse suspension copolymerization of acrylic acid and sodium acrylate.

A saturated aqueous solution of sodium chloride is prepared and found to contain about 29 weight percent of sodium chloride. To 60.08 grams of the saturated sodium chloride solution is added with mixing, 0.10 grams of hydrogen peroxide. The resulting solution is dripped into a three-neck, 1,000 milliliter round-bottomed flask to which 602.51 grams of toluene and 12.25 grams of ethyl cellulose have been added, in that respective order under a nitrogen gas purge. The contents of the round-bottomed flask are maintained under a nitrogen gas purge throughout the polymerization process.

A sodium hydroxide solution is prepared by mixing 84.12 grams of distilled water with 15.04 grams of sodium hydroxide in a beaker immersed in an ice bath. To the sodium hydroxide solution is added, by single drops, 36 grams of acrylic acid to form a monomer solution. To this monomer solution is added 0.77 grams of methylene bisacrylamide and 0.05 grams of L (+) ascorbic acid. The monomer solution is then transferred to a graduated burette and added to the well-agitated round-bottomed flask over a period of forty-eight minutes. The round-bottomed flask is then stirred, while being maintained at 40° C., for an additional sixty-five minutes. The contents of the flask are then raised to 87° C. and the water azeotropically distilled from the round-bottomed flask. The particles remaining in the flask are then removed and dried overnight at 90° C.

Figure 4A:
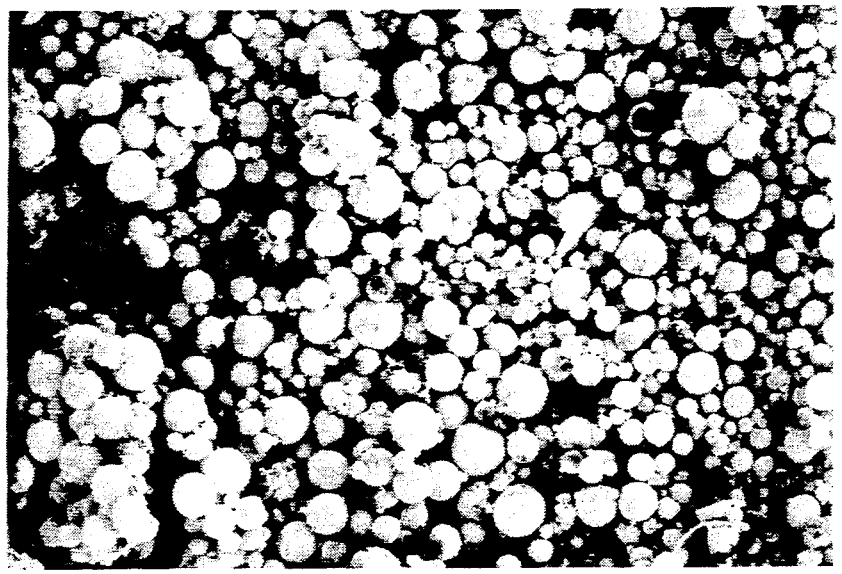
FIGS. 4a–c are photomicrographs of the embodiment of the present invention taken at different degrees of magnification (25X, 100X, 5000X).
Figure 4B:
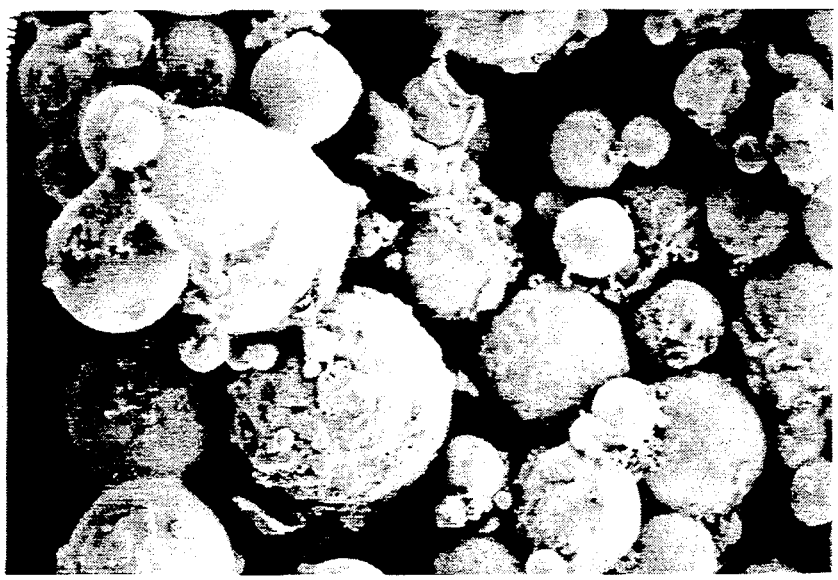
Figure 4C:

The particles so produced are believed to comprise a generally solid core of sodium chloride which core is generally completely surrounded by the copolymeric material. FIGS. 4a–4c are scanning electron micrographs of the resultant particles taken at magnifications of 25X, 100X, and 5000X, respectively. Reference to FIGS. 4a–4c reveals that the particles are generally spheroidal in shape.

The resulting particles and particle agglomerates are then screened on U.S. standard size screens, and those particle passing through a #30 mesh and retained on a #50 mesh (300–600 microns) are subjected to various physical property determinations.

The absorbent capacity of the particles on a gram per gram basis is determined by soaking 0.5 grams of the particles in an excess of an aqueous solution containing 0.9 weight percent sodium chloride for 60 minutes. The slurry of particles and sodium chloride solution is then poured through a 45 mesh sieve into a tared beaker. The swollen particles (gel) retained on the sieve are stirred to aid drainage and finally shaken to remove excess fluid. The absorbent capacity is calculated from the weights of the filtrate ($f$), gel ($W_g$), dry polymer ($W_p$) and initial solution ($W_s$) according to the following formula:

$$\frac{(W_s - W_f) + (W_g - 0.5)}{2(W_p)}$$

It is desireable to determine if a significant amount of the salt (in this case sodium chloride) which is believed to form the core of the particles, diffuses out of the particle during swelling of the particles, or if a significant number of the particles burst upon swelling. Accordingly, conductivity of the solution and filtrate from the determination of absorption capacity is measured using a YSI model 32 conductivity meter commercially available from Scientific Division Yellow Springs Instrument and Co., Inc. As the salt concentration in a solution increases, the conductivity of the solution increases. Thus, if the conductivity of the filtrate is significantly higher than the conductivity of the initial solution, it can be inferred that additional salt from the core of the particles has passed out of the particles either by diffusion or by rupture of the particles.

Figure 5:
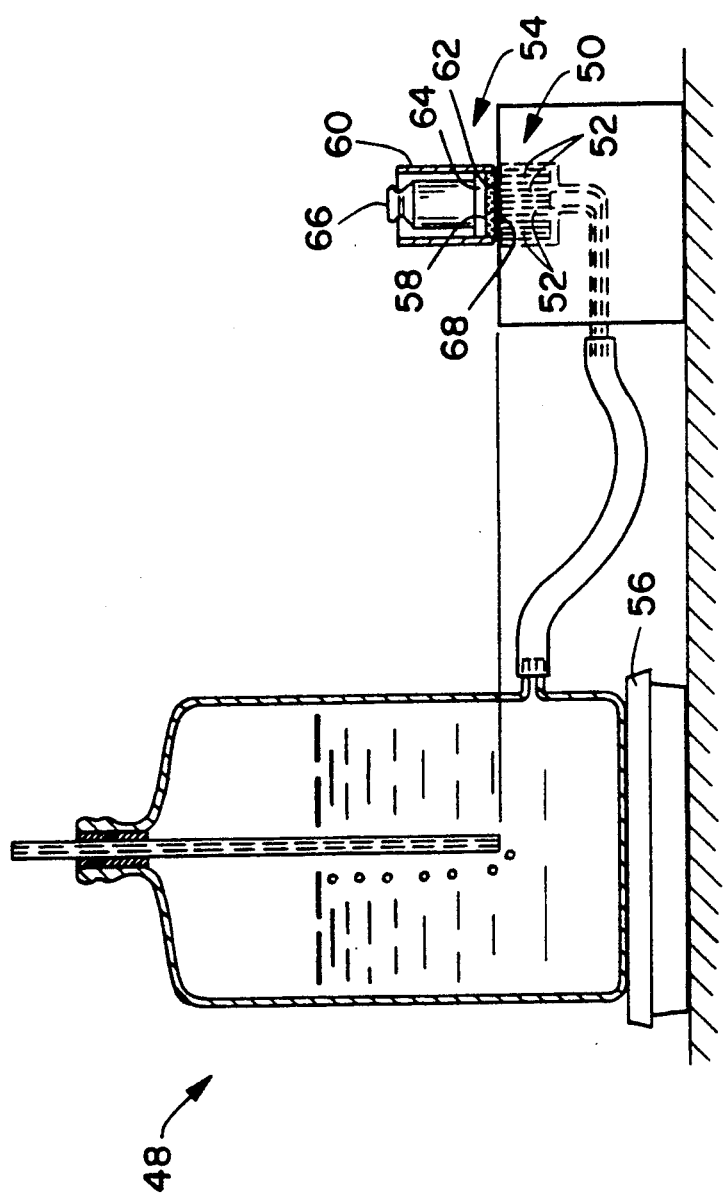
FIG. 5 is an illustration of the test apparatus employed to determine the absorbency under load of structures according to the present invention.

The ability of the particles to absorb a liquid while under a restraining force (absorbency under load, hereinafter AUL) is determined as follows. Referring to FIG. 5, a Demand Absorbency Tester (DAT) 48 is used, which is similar to a GATS (Gravimetric Absorbency Test System), available from M/K Systems, Danners Mass., as well as the system described by Lichstein at pages 129–142 of the INDA Technological Symposium Proceedings, March 1974. A porous plate 50 is used having ports 52 confined within a 2.5 centimeter diameter area and covered by the absorbency under load (AUL) apparatus 54. An electro balance 56 is used to measure the flow of fluid, normally 0.9 (w/w)% sodium chloride into the superabsorbent particles 58.

The special apparatus 54 used to contain the superabsorbent particles comprises a cylinder 60 made from one inch (2.54 centimeter) inside diameter thermoplastic tubing which is machined-out slightly to be sure of concentricity. A 100 mesh stainless steel wire cloth 62 is fused on the bottom of cylinder 60 by heating the wire cloth in a flame until red hot after which the cylinder is held onto the cloth until cooled. A soldering iron can be utilized to touch up the seal if unsuccessful or it breaks. Care must be taken to maintain a flat smooth bottom and not distort the inside of the cylinder. A 4.4 gram piston 64 is made from one inch diameter solid material (e.g., Plexiglas TM) and is machined to closely fit without binding in the cylinder 60. A standard 100 gram weight 66 is used to provide about 0.3 pounds per square inch restraining load which is commonly experienced in infant diapers. Unless specified otherwise, a sample of superabsorbent particles weighing 0.16 grams is utilized for testing AUL. The sample is taken from granules which are pre-screened through U.S. standard #30 mesh and retained on U.S standard #50 mesh (300 to 600 microns).

This test is initiated by placing a 3 centimeter diameter GF/A glass filter paper 68 onto the plate 50, (the paper is sized to be larger than the internal diameter and smaller than the outside diameter of the cylinder 60, to insure good contact while eliminating evaporation over the ports 52 of the DAT 48 and then allowing saturation to occur. The desired amount of particles 58 (about 0.16 grams) is weighed out on a weigh paper and placed on the wire cloth 62 at the bottom of the AUL apparatus 54. The apparatus 54 is shaken to level the particles 58 on the wire cloth 62. Care is taken to be sure no particles are clinging to the wall of the cylinder 60. After carefully placing the piston 64 and weight 66 on the particles 58 in the cylinder 60, the AUL apparatus 54 is placed on the glass filter paper 68. The amount of fluid pick-up is monitored as a function of time either directly by hand, with a strip chart recorder or directly into a data acquisition or personal computer system.

The amount of fluid pickup measured after one hour is the AUL value. The rate of fluid pickup can also be measured. Two checks can be made to insure the accuracy of the instantaneous final readout. First, the height the piston 64 rises multiplied by the cross-sectional area of the cylinder 60 should nearly equal the amount of fluid picked up. Second, the AUL apparatus 54 can be weighed before and after the test, and the difference in weight should nearly equal the fluid picked up.

The rate at which the particles are able to absorb a fluid is determined as set forth above in connection with determining the AUL value. For example, fluid pickup can be determined at 10 minutes and 60 minutes and the rate of pickup determined therefrom.

A control sample of particles is prepared according to the method set forth above except that sodium chloride is not added to the solution to which the hydrogen peroxide is added. The particles so produced are subjected to the same physical property testing described above.

The results of the various physical property testing described above are set forth in Table I.

EXAMPLE 2

Absorbent structures according to the present invention are produced through the inverse suspension copolymerization of acrylic acid and sodium acrylate similar to the process of Example I except that calcium chloride is added to the saturated sodium chloride solution. The presence of the calcium ion is believed to induce the formation of complexes within the copolymer thus rendering the copolymer less water-swellable than copolymer produced in the absence of the calcium ion.

A saturated aqueous solution of sodium chloride and calcium chloride is prepared and found to contain about 25.2 weight percent of sodium chloride and about 3.0 weight percent calcium chloride. To 60.0 grams of the saturated sodium chloride/calcium chloride solution is added with mixing, 0.1564 grams of hydrogen peroxide. The resulting solution is dripped into a three-neck 1,000 milliliter round bottomed flask to which 600.62 grams of toluene and 12.01 grams of ethyl cellulose have been added, in that respective order under a nitrogen gas purge. The contents of the round-bottomed flask are maintained under a nitrogen gas purge throughout the polymerization process.

A sodium hydroxide solution is prepared by mixing 84.03 grams of distilled water with 15.02 grams of sodium hydroxide in a beaker immersed in an ice bath. To the sodium hydroxide solution is added, by single drops, 36.01 grams of acrylic acid to form a monomer solution. To this monomer solution is added 0.7738 grams of methylene bisacrylamide and 0.0506 grams of L (+) ascorbic acid. A mass of 100.37 grams of the monomer solution is then transferred to a graduated burette and added to the round-bottomed flask over a period of forty-eight minutes. The round-bottomed flask is stirred while being maintained a 40° C. for an additional sixty-five minutes. The contents of the flask are then raised to 87° C. and the water azeotropically distilled from the round bottomed flask. The particles remaining in the flask are then removed and dried overnight at 90° C.

The particles and agglomerated particles are then screened as set forth in Example 1 to isolate those particles having a diameter between about 300 and about 600 microns. These particles and agglomerated particles are then subjected to physical property testing. The absorbent capacity, AUL, absorption rate, and diffusion of the osmotic material, as measured by conductivity, are then determined according to the procedures set forth in Example 1. The results of this testing are set forth in Table 1.

The control sample of particles prepared as set forth in connection with Example 1 is a suitable control for the present Example.

TABLE I

| | Capacity[1] | AUL 10 Min. | AUL 60 Min. | Conductivity |
|---|---|---|---|---|
| Example #1 (solution) | 44.2 | 20.0 | 30.0 | 13.0 mv |
| (filtrate) | | | | 12.0 mv |
| Example #2 (solution) | 15.9 | 5.5 | 6.2 | 14.5 mv |
| (filtrate) | | | | 17.4 mv |
| Control (solution) | 3.5 | 1.9 | 1.3 | 14.7 mv |
| (filtrate) | | | | 14.4 mv |

[1]Capacity in grams of absorbed solution per gram of polymer.

As can be seen from reference to Table I, the particles according to the present invention are superior in absorbent capacity, absorption rate and AUL when compared to the control samples. Moreover, it is seen from the conductivity determinations that sodium chloride present in the particles according to the present invention does not appear to be reaching the solution in which the particles are allowed to swell.

EXAMPLE 3

The following test samples are prepared from a thermoplastic superabsorbent material prepared according to U.S. Pat. No. 4,767,825, issued Aug. 30, 1988, to Pazos et al., the teachings of which are incorporated herein by reference. The specific superabsorbent material employed is a linear polymer formed from chain extending 8000 molecular weight poly (ethylene oxide) with 1,4-butanediol and methylene diisocyanate (96 weight percent poly (ethyleneoxide)). This polymer is found to be soluble in 1,1,1-trichloroethylene to form a viscous dope at a concentration of 10 weight percent polymer.

A variety of osmotic materials according to the present invention are provided in the form of discrete particles. The particles are weighed, to the nearest 0.1 mg and coated with the superabsorbent material dope described above. The coated particles are then dried. The specific osmotic materials employed are:

A bead of 1-triacontanol having a diameter of about 2000 microns;

A spherical urea pill having a diameter of about 2000 microns;

An irregularly shaped granule of aluminum sulfate having a diameter of about 1000 microns; and A granule of sucrose having a diameter of about 2000 microns formed by agglomerating small particles of sucrose and drying.

A first control sample, Control A, of the superabsorbent material is formed by casting a film of the superabsorbent material on glass from the 10 weight percent solution of the superabsorbent material in 1,1,1-trichloroethylene. The superabsorbent film is formed into a sphere while still tacky with solvent. The sphere has a diameter of about 1000 microns. A second control sample, Control B, is formed by coating a bead of paraffin-extended polyethylene with the 10 weight percent solution of superabsorbent material in 1,1,1,-trichloroethylene. The bead of paraffin-extended polyethylene has a diameter of about 2000 microns.

The coated particles of osmotic material and the controls are then weighed to the nearest 0.1 mg. The coated particles and controls are then placed in an aqueous sodium chloride solution containing 1 percent, by weight, sodium chloride. The test samples are allowed to remain in the sodium chloride solution until no further weight gain is observed (30 to 60 minutes). That is, until the samples have essentially reached their maximum absorbent capacity. The swollen test samples are then blotted on paper towels to remove any clinging water and weighed. The absorbent capacity is calculated by subtracting the dry weight of the coated particle from the weight of the swollen test sample and dividing by the weight of the polymer present in the particle. The weight of polymer present in the particles is determined by subtracting the weight of the uncoated osmotic material from the coated particles (prior to swelling). The results of this test are set forth in Table 2.

TABLE 2

| Osmotic Agent | Core[1] | Shell[1] | Gel[1] | Capacity[2] | Increase[3] |
|---|---|---|---|---|---|
| 1-triacontanol | 9.7 | 3.6 | 101.2 | 24.4 | 97 |
| 1-triacontanol | 6.8 | 1.5 | 46.0 | 25.1 | 103 |
| 1-triacontanol | 6.5 | 1.9 | 67.7 | 31.2 | 152 |
| 1-triacontanol | 10.5 | 3.2 | 120.9 | 33.5 | 170 |
| Urea | 6.9 | 0.8 | 23.9 | 20.2 | 63 |
| Aluminum Sulphate | 4.2 | 1.1 | 24.7 | 16.1 | 30 |
| Sucrose | 8.7 | 2.4 | 76.7 | 27.3 | 120 |
| Control A | 0.0 | 5.3 | 70.9 | 12.4 | N/A |
| Control B | 5.8 | 5.4 | 82.4 | 13.1 | 6 |
| Control B | 7.4 | 4.9 | 74.8 | 12.7 | 2 |

TABLE 2-continued

| Osmotic Agent | Core[1] | Shell[1] | Gel[1] | Capacity[2] | Increase[3] |
|---|---|---|---|---|---|
| Control B | 8.4 | 4.5 | 83.4 | 15.7 | 26 |
| Control B | 5.9 | 7.0 | 102.5 | 12.8 | 3 |

[1] Weight in milligrams.
[2] In grams of liquid absorbed per gram of polymer.
[3] Percent increase of capacity compared to control A.
N/A Not applicable.

As can be seen from reference to Table 2, the presence of an osmotic material within the chamber defined by the superabsorbent polymer enhances the absorptive capacity of the superabsorbent material on a gram per gram basis. None of the control samples consistently achieved the degree of improvement achievable with the osmotic materials according to the present invention.

EXAMPLE 4

The superabsorbent material employed in this example is prepared from a terpolymer of ethyl acrylate, sodium acrylate, and sodium methacrylate, which terpolymer is commercially available from the Dow Chemical Company, Midland, Michigan, under the trade designation XD-8587.01. To be converted into a superabsorbent material the terpolymer must be crosslinked. The crosslinking agent employed is a polyamidoamine epichlorohydrin resin commercially available from Hercules Inc., Wilmington, Del., under the trade designation Kymene 557. The crosslinking is accomplished according to the method described in U.S. Pat. No. 3,926,891, issued Dec. 16, 1975, to Gross et al., the teachings of which are incorporated herein by reference. Essentially, the crosslinking process involves mixing the terpolymer with 5 weight percent of the crosslinking agent to form a curable polymer solution. The curable polymer solution is then dried at an elevated temperature to remove water and initiate crosslinking.

Again, as in Example 3, various osmotic materials are employed and are provided in the form of discrete particles. The particles are weighed, to the nearest 0.1 mg and coated with the curable polymer solution described above (prior to drying and crosslinking). The surface of the coated particles is hardened by dropping the coated particles in acetone. The particles are then dried in a 40° C. oven for three hours. It is during the drying process that crosslinking of the terpolymer takes place. The specific osmotic materials employed are:

A spherical urea pill having a diameter of about 2000 microns; and

A granule of sucrose having a diameter of about 2000 microns formed by agglomerating small particles of sucrose and drying.

As a control, a drop of the curable solution used to coat the osmotic materials is dropped in acetone to harden its surface and is then dried as described above.

The coated particles of osmotic material and the control are then weighed to the nearest 0.1 mg. The coated particles and control are then placed in an aqueous sodium chloride solution containing 1 percent, by weight, sodium chloride. The test samples are allowed to remain in the sodium chloride solution until no further weight gain is observed (60 to 120 minutes). That is, until the samples have essentially reached their maximum absorbent capacity. The swollen test samples are then blotted on paper towels to remove any clinging water and weighed. The absorbent capacity is calculated by subtracting the dry weight of the coated particle from the weight of the swollen test sample and dividing by the weight of the polymer present in the particle. The weight of polymer present in the particles is determined by subtracting the weight of the uncoated osmotic material from the coated particles (prior to swelling). The results of this test are set forth in Table 3.

TABLE 3

| Osmotic Agent | Core[1] | Shell[1] | Gel[1] | Capacity[2] | Increase[3] |
|---|---|---|---|---|---|
| Urea | 14.5 | 2.0 | 123.9 | 53.7 | 215 |
| Sucrose | 14.3 | 4.8 | 168.4 | 31.1 | 82 |
| Sucrose | 8.9 | 1.1 | 75.6 | 59.6 | 250 |
| Sucrose | 10.0 | 1.0 | 77.4 | 66.4 | 289 |
| Control | 0.0 | 10.8 | 196.0 | 17.1 | N/A |
| Control | 0.0 | 4.4 | 79.1 | 17.0 | N/A |

[1]Weight in milligrams.
[2]In grams of liquid absorbed per gram of polymer.
[3]Percent increase of capacity compared to control.
N/A Not applicable.

As can be seen from reference to Table 3, the presence of the osmotic material within the chamber formed by the superabsorbent material significantly improves the absorptive capacity of the superabsorbent material on a gram per gram basis. Indeed, improvements of up to 289 percent are demonstrated.

EXAMPLE 5

An example of an absorbent structure according to the present invention which structure is i the shape of a fiber is prepared in the following manner. The superabsorbent material employed in this example is the thermoplastic superabsorbent material employed in example 3. The superabsorbent material is formed into a cylinder having a length of 3 centimeters and a diameter of 0.75 centimeters. The cylinder is then partially hollowed out to form a hollow cylinder. The hollow cylinder has an internal diameter of about 0.32 centimeter. To the interior of the hollow cylinder is charged 0.184 grams of sodium chloride. The open end of the sodium chloride-filled cylinder is then sealed by melting the surrounding polymer.

A control sample is prepared in the manner set forth above except that the hollow cylinder is not filled with sodium chloride prior to sealing the end of the cylinder.

The sodium chloride-filled cylinder and the control cylinder are then placed in an excess of an aqueous sodium chloride solution containing 1 percent, by weight, of sodium chloride. The cylinders are allowed to remain in the sodium chloride solution until no additional weight gain is measured (the cylinders have essentially reached their maximum capacity). The cylinders are then removed from solution and weighed. The absorptive capacity of the sodium chloride-filled cylinder is determined to be about 21.0 grams of liquid per gram of polymer. The absorptive capacity of the control cylinder is determined to be about 6.0. grams of liquid per gram of polymer. Thus, the presence of the osmotic material in the cylinders is found to produce an increase in absorptive capacity of about 250 percent.

EXAMPLE 6

An example of an absorbent structure according to the present invention which structure is in the shape of a fiber is prepared as described in connection with example 5. A control sample containing no sodium chloride is also prepared. The salt filled fiber and control are then subjected to the test method set forth above in order to determine the absorption capacity of the fibers. However, in order to determine the effect on rate, the fibers are removed from the sodium chloride solution at various times and the fluid absorption noted. The fluid pickup is reported as a function of time in Table 4.

TABLE 4

| | NaCl Filled Fibers | | Control | |
|---|---|---|---|---|
| Time[1] | Absorption[2] | Rate[3] ($\times 10^{-2}$) | Absorption[2] | Rate[3] ($\times 10^{-2}$) |
| 0 | 0 | — | 0 | — |
| 30 | 1.85 | 6.17 | 1.63 | 5.43 |
| 60 | 2.8 | 3.17 | 2.36 | 2.43 |
| 120 | 7.5 | 7.83 | 3.39 | 1.72 |
| 180 | 10.1 | 4.33 | 4.54 | 1.92 |
| 240 | N/D | — | 5.52 | 1.63 |
| 300 | 16.4 | 5.25 | 6.23 | 1.18 |
| 360 | N/D | — | 6.98 | 1.25 |
| 480 | 20.3 | 2.17 | N/D | — |
| 1440 | 23.1 | 0.29 | 12.91 | 0.55 |

N/D = Not determined
[1] = Time in minutes.
[2] = Absorption in grams of liquid absorbed per gram of polymer.
[3] = Rate in grams of liquid absorbed per gram of polymer per minute.

As can be seen from reference to table 4, both the capacity and the rate of pickup for the NaCl filled fibers is significantly improved when compared to the control sample. While the last rate value for the control is higher tan the corresponding value for the filled fibers, this is due to the fact that the control (due to its lower rate) absorbed about 46 percent of its 1440 minute capacity in the period from 480 minutes to 1440 minutes, while the filled fibers (due to its high rate) absorbed only about 12 percent of its 1440 minute capacity in the period from 480 minutes to 1440 minutes.

EXAMPLE 7

In this example, a porous urea-formaldehyde condensation polymer is employed as the osmotic material. The urea-formaldehyde polymer is highly hydrophilic but generally water-insoluble. The urea-formaldehyde polymer is prepared as follows. Thirty (30) grams of a urea-formaldehyde formaldehyde prepolymer commercially available from Borden Chemical under the trade designation UF-72 is added to a hexane solution containing 5 weight percent sorbitan monolaurate which has been reacted with 5 moles of ethylene oxide (commercially available from ICI Americas, Inc. under the trade designation Tween 21 ™). The urea-formaldehyde prepolymer has a urea to formaldehyde ratio of 1.5 to 1.0 and is in the form of a 50 percent solids dispersion.

The hexane/prepolymer emulsion is stirred at room temperature until discrete droplets are formed and is then partially polymerized by the slow addition of 0.5 grams of a 60 percent aqueous solution of phenolsulfonic acid. The partially polymerized product is diluted in a 20 percent sodium sulfate solution to break the emulsion which causes discrete microporous, microparticles of urea formaldehyde to form which are recovered by filtration and dried under vacuum.

The dried microparticles are dispersed in a 2 percent solution of calcium carrageenan and locust bean gums to deposit a swellable coating on the particles. The coated particles are filtered and dried. The resultant coated particles are subjected to physical property determinations. The absorptive capacity of the coated particles is determined by allowing the particles to stand in an excess of synthetic urine for 30 minutes at 100° C. The synthetic urine employed is produced as follows. To 900 milliliters of distilled water are added, in the following order, 0.31 grams of monobasic calcium phosphate monohydrate (CaH$_4$(PO$_4$)$_2$H$_2$O), 0.68 grams monobasic potassium phosphate (KH$_2$PO$_4$), 0.48 grams magnesium sulphate heptahydrate (MgSO$_4$.7-H$_2$O), 1.33 grams potassium sulphate (K$_2$SO$_4$), 1.24 grams tribasic sodium phosphate dodecahydrate (Na$_3$PO$_4$.12H$_2$O), 4.4 grams sodium chloride (NaCl), 3.16 grams potassium chloride (KCl), 0.4 grams sodium azide (NaN$_3$), 8.56 grams urea (CO(NH$_2$)$_2$), and 0.1 grams pluronic 10R8 (a non-ionic surfactant commercially available from BASF-Wyandotte Corporation). Each of the components is added to the 900 milliliters of distilled water in the order given with each component being dissolved before the next component is added. The resulting solution is then diluted to 1 liter.

The microparticles are found to agglomerate upon swelling and are found to have an absorptive capacity of 18 grams of synthetic urine per gram of dry microparticles. The microparticles have a diameter of about 30 microns. The microparticles so produced are desireable because they employ an osmotic material which is not extractable by the absorbed liquid. That is, the urea-formaldehyde polymer is not soluble in the synthetic urine.

EXAMPLE 8

A urea-formaldehyde prepolymer having a urea to formaldehyde ratio of 1 to 1 is catalyzed with dodecylbenzene sulfonic acid and mixed with a nonsolvent such as tetrahydrofuran or acetonitrile-dioxane to form discrete particles which are isolated and dried. The resultant particles are dispersed in a 2 percent solution of xanthan gum to deposit a swellable coating on the particles. The coated particles are recovered and dried. The absorptive capacity of the particles is determined as set forth in connection with example 7. The particles are found to have a capacity of 13 grams of synthetic urine per gram of dry polymer.

WHAT IS CLAIMED IS

1. An absorbent structure, said absorbent structure comprising a superabsorbent material, said superabsorbent material defining a chamber substantially void of said superabsorbent material, said chamber containing an amount of an osmotic material.

2. The absorbent structure according to claim 1, wherein the superabsorbent material is selected from the group consisting of gelatin; alginates; cellulose based polymers such as methyl cellulose, hydroxymethyl cellulose, carboxymethylcellulose, cellulose acetate phthalate, and the like; starch based polymers such as carboxymethyl starch; natural gums, such as gum arabic, locust bean gum, carrageenan gum and xanthan gum; pectins; polymers formed from acid-group containing monomers, such as poly(acrylates) (including poly(acrylic acid), poly(methacrylic acid), and the like), poly(ethers), poly(acrylamides), poly(vinyl alcohol), maleic anhydride copolymers, poly(vinyl sulfonates), hydrolyzed acrylonitrile grafted starch, acrylic acid grafted starch, poly(N-vinyl pyrrolidone), poly (2-hydroxyethylacrylate), poly(2-hydroxyethylmethacrylate), poly (sodium acrylate-co-acrylic acid), poly(vinylsulfonic acid), poly (ethyleneoxide), block co-polymers of ethylene oxide with polyamides, polyesters, and polyurethanes, and salt forms mixtures and copolymers of the above.

3. The absorbent structure according to claim 2 wherein the superabsorbent material is selected from the group consisting of poly (acrylates).

4. The absorbent structure according to claim 2 wherein the superabsorbent material is a block copolymer of ethylene oxide and polyurethane.

5. The absorbent structure according to claim 1 wherein the osmotic material has a relative osmosity of at least about 0.05.

6. The absorbent structure according to claim 5 wherein the osmotic material has a relative osmosity of at least about 0.09.

7. The absorbent structure according to claim 5 wherein the osmotic material is selected from the group consisting of water-soluble or water-dispersible salts of organic or inorganic acids, organic or inorganic acids, long chain alcohols, polyhydric alcohols, urea and urea derivatives, mono- or oligosaccharides, water-soluble polymers, and surfactants.

8. The absorbent structure according to claim 6 wherein the osmotic material is selected from the group consisting of organic or inorganic acids, water soluble salts of organic or inorganic salts, urea and urea derivatives and mono-or oligosaccharides.

9. The absorbent structure according to claim 1 wherein the ratio of the volume of the chamber to the volume of the absorbent structure, including the chamber, is from about 1:10 to about 999:1000.

10. The absorbent structure according to claim 9, wherein the ratio of the volume of the chamber to the volume of the absorbent structure, including the chamber, is from about 1:2 to about 9:10.

11. The absorbent structure according to claim 1, wherein the ratio of the volume of osmotic material present in the chamber to the volume of the chamber is from about 1:100 to about 1:1.

12. The absorbent structure according to claim 11, wherein the ratio of the volume of osmotic material present in the chamber to the volume of the chamber is from about 1:20 to about 1:1.

13. The absorbent structure according to claim 11 wherein the chamber is not completely filled with osmotic material and the ratio of the volume of osmotic material present in the chamber to the volume of the chamber is from about 1:100 to about 99:100.

14. The absorbent structure according to claim 1 wherein the structure is in the form of a sphere or an irregularly shaped article having an average diameter within the range of from about 1 to about 4000 microns.

15. The absorbent structure according to claim 14 wherein the sphere or irregularly shaped article has an average diameter within the range of from about 50 to about 1000 microns.

16. The absorbent structure according to claim 1 wherein the structure is in the form of a fiber having a length to diameter ratio of at least about 5:1.

17. The absorbent structure according to claim 7 wherein the osmotic material is not water-soluble.

18. The absorbent structure according to claim 1 wherein the structure is formed through an inverse suspension polymerization process.

19. An absorbent product, said product comprising:
a fibrous matrix; and
an absorbent structure dispersed in said fibrous matrix, said absorbent structure comprising a superabsorbent material, said superabsorbent material defining a chamber substantially void of said superabsorbent material, said chamber containing an amount of an osmotic material.

20. The absorbent product of claim 19, wherein the absorbent product is a diaper, said diaper further comprising a water-pervious body-side liner adapted to contact the skin of a wearer, and a water-impervious outer backing, said fibrous matrix being sandwiched between said body-side line and said outer backing.

21. The absorbent product of claim 19 wherein the absorbent structure is present in said matrix in an amount of from about 5 to about 50 weight percent, based on total weight of the fibrous matrix and absorbent structure.

22. The absorbent structure according to claim 1 wherein said superabsorbent material is capable of absorbing at least about 5 times its weight in water.

23. The absorbent structure according to claim 1 wherein said superabsorbent material is capable of absorbing at least about 20 times its weight in water.

24. The absorbent structure according to claim 2 wherein said superabsorbent material is capable of absorbing at least about 20 times its weight in water.

25. The absorbent product according to claim 19 wherein said superabsorbent material is capable of absorbing at least about 5 times its weight in water.

26. The absorbent product according to claim 19 wherein said superabsorbent material is capable of absorbing at least about 20 times its weight in water.

27. An absorbent structure, said absorbent structure comprising a superabsorbent material, said superabsorbent material defining a chamber substantially void of said superabsorbent material, said chamber containing an amount of an osmotic material, wherein said superabsorbent material is capable of absorbing at least about 5 times its weight in water and wherein the superabsorbent material is selected from the group consisting of gelatin; alginates; starch-based polymers such as carboxymethyl starch; natural gums; such as gum arabic, locust bean gum, carrageenan gum and xanthan gum; pectins; polymers formed from acid-group containing monomers, such as poly(acrylates) (including poly(acrylic) acid), poly(methacrylic acid), and the like), poly(ethers), poly(acrylamids), poly(vinyl alcohol), maleic anhydride copolymers, poly(vinyl sulfonates), hydrolyzed acrylonitrile grafted starch, acrylic acid grafted starch, poly(N-vinyl pyrrolidone), poly(2-hydroxyethylacrylate), poly(2-hydroxyethyl-methacrylate), poly(sodium acrylate-co-acrylic acid), poly(vinyl sulfonic acid), poly(ethylene oxide), block co-polymers of ethylene oxide with polyamides, polyesters, and polyurethanes, and salt forms, mixtures and copolymers of the above.

28. The absorbent structure according to claim 27 wherein said superabsorbent material is capable of absorbing at least about 20 times its weight in water.

29. An absorbent product, said product comprising:
a fibrous matrix; and
an absorbent structure according to claim 27 dispersed in said fibrous matrix.

* * * * *